US008022077B2

(12) United States Patent
Simmen et al.

(10) Patent No.: US 8,022,077 B2
(45) Date of Patent: Sep. 20, 2011

(54) PYRIDO[2,3-D]PYRIMIDINES USEFUL AS HCV INHIBITORS, AND METHODS FOR THE PREPARATION THEREOF

(75) Inventors: Kenneth Alan Simmen, Tervuren (BE); Dominique Louis Nestor Ghislain Surleraux, Braine-le-château (BE); Tse-I Lin, Mechelen (BE); Oliver Lenz, Sint-Katelijne-Waver (BE); Pierre Jean-Marie Bernard Raboisson, Sterrebeek (BE)

(73) Assignee: Tibotec Pharmaceuticals Ltd., Little Island, Co Cork (IE)

( * ) Notice: Subject to any disclaimer, the term of this patent is extended or adjusted under 35 U.S.C. 154(b) by 0 days.

(21) Appl. No.: 11/914,044

(22) PCT Filed: May 12, 2006

(86) PCT No.: PCT/EP2006/062290
§ 371 (c)(1),
(2), (4) Date: Jun. 20, 2008

(87) PCT Pub. No.: WO2006/120252
PCT Pub. Date: Nov. 16, 2006

(65) Prior Publication Data
US 2009/0131460 A1 May 21, 2009

Related U.S. Application Data
(60) Provisional application No. 60/680,405, filed on May 12, 2005.

(30) Foreign Application Priority Data
Jul. 7, 2005 (EP) .................................. 05106214
Apr. 6, 2006 (EP) .................................. 06075855

(51) Int. Cl.
C07D 471/04 (2006.01)
A61K 31/519 (2006.01)
A61P 1/16 (2006.01)
A61P 31/12 (2006.01)
(52) U.S. Cl. ................. 514/264.1; 514/264.11; 544/279
(58) Field of Classification Search .................. 544/279; 514/264.1, 264.11
See application file for complete search history.

(56) References Cited

U.S. PATENT DOCUMENTS
3,873,545 A 3/1975 Osselaere et al.
2004/0038856 A1 2/2004 Chakravarty et al.

FOREIGN PATENT DOCUMENTS
JP 2003321472 11/2003
WO WO 95/19774 A1 7/1995
WO WO 00/12497 A2 3/2000
WO WO 03/059913 A1 7/2003
WO WO 03/097615 A1 11/2003
WO WO 2004/020584 A3 3/2004
WO WO 2004/074270 A2 9/2004
WO WO 2005/032481 A3 4/2005
WO WO 2006/100310 A1 9/2006
WO WO 2006105063 * 10/2006

OTHER PUBLICATIONS
De Mitri, et al., Lancet 1995:345:413 (Abst.).*
Sekiguchi, et al., World J. Gastroentrol., Apr. 7, 2006, 12(13), 2089-2094.*
Breipohl et al., "Novel Synthetic Routes to PNA Monomers and PNA-DNA Linker Molecules", Tetrahedron vol. 53, No. 43, pp. 14671-14686 (1997).
Choo, et al., "Isolation of a cDNA Clone Derived from a Blood-Borne Non-A, Non-B Viral Hepatitis Genome", Science, vol. 244, pp. 359-362, (1989).
Cywin, et al., "Discovery and SAR of Novel [1,6]Naphthyridines as Potent Inhibitors of Spleen Tyrosine Kinase (SYK)" Bioorganic and Medicinal Chemistry Letters, vol. 13, No. 8, pp. 1415-1418 (2003).
Goodman and Gilman, The Pharmacological Basis of Therapeutics, 8[th]ed, McGraw-Hill, Int. Ed., "Biotransformation of Drugs", pp. 13-15 (1992).
Harrison, D. et al., "Synthesis of Some Cyclic Hydroxamic Acides from—Aminocarboxylic Acids", Journal of the Chemical Society Abstracts, XP002373945, Database accession No. 1960:118360, pp. 2157-2160 (1960).
Kim, W.R., "The Burden of Hepatitis C in the United States", Hepatology, vol. 36, No. 5. suppl. 1, pp. S30-S34, (2002).
Kolykhalov, A.A., et al., "Hepatitis C Virus-Encoded Enzymatic Activities and Conserved RNA Elements in the 3' Nontranslated Region are Essential for Virus Replication in Vivo", Journal of Virology, vol. 74, No. 4, pp. 2046-2051 (2000).
Krieger et al., "Enhancement of Hepatitis C Virus RNA Replication by Cell Culture-Adaptive Mutations" Journal of Virology, vol. 75, No. 10, pp. 4614-4624 (2001).

(Continued)

Primary Examiner — James O Wilson
Assistant Examiner — Cecilia M Jaisle
(74) Attorney, Agent, or Firm — Andrea Jo Kamage

(57) ABSTRACT

The present invention relates to the use of pyrido[2,3-d]pyrimidines of formula (I)

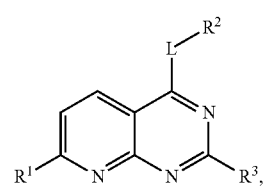

wherein L, $R^1$, $R^2$ and $R^3$ have specific meaning. The present invention also relates to the use of the compounds of formula (I) as inhibitors of HCV replication as well as their use in pharmaceutical compositions aimed to treat or combat HCV infections. In addition, the present invention relates to compounds of formula (I) per se and their use as medicines. The present invention also concerns processes for the preparation of such compounds, pharmaceutical compositions comprising them, and combinations of said compounds with other anti-HCV agents.

22 Claims, No Drawings

OTHER PUBLICATIONS

Lauer, G.M. and Walker, B.D., "Hepatitis C Virus Infection", The New England Journal of Medicine, vol. 345, No. 1, pp. 41-52 (2001).

Lohmann et al., "Replication of Subgenomic Hepatitis C Virus RNAs in a Hepatoma Cell Line", Science, vol. 285, pp. 110-113 (1999).

Nishikawa, Shiro et al., "Cytokinin Activity of 4-Aminopyrimidines toward the Growth of Tobacco Callus", Bioscience, Biotechnology and Biochemistry, vol. 58(9), pp. 1709-1710(1994).

Warnhoff, H., et al., "Dihalogentriphenylphosphorane in der Heterocyclensynthese 29.1 Eine einfache Synthese von Pteridin-4-onen aus 3-Amino-2-pyrazincarbonsauremethylester und Pyrazino[3,1]oxazin-3-onen", Synthesis, pp. 405-410, (1994).

Vercek, et al., Neighboring Group Interaction in Orthio-Substituted Heterocycles.2.1,2,4,-Oxadiazolypyridines and Pyridol[2,3,-d]pyrimidine 3-Oxides Journal of Organic Chemistry, vol. 44, No. 10, pp. 1695-1699 (1979).

National Institutes of Health Consensus Development Conference Statement: Management of Hepatitis C, Hepatology, 36, 5 Suppl. S3-S20, (2002).

* cited by examiner

PYRIDO[2,3-D]PYRIMIDINES USEFUL AS HCV INHIBITORS, AND METHODS FOR THE PREPARATION THEREOF

The present invention relates to the use of pyrido[2,3-d] pyrimidines as inhibitors of HCV replication as well as their use in pharmaceutical compositions aimed to treat or combat HCV infections. In addition, the present invention relates to compounds per se. The present invention also concerns processes for the preparation of such compounds, pharmaceutical compositions comprising them, and combinations of said compounds with other anti-HCV agents.

Following its discovery in 1989 as the agent implicated in the majority of viral non-A, non-B hepatitis (Choo et al., Science 244, 359-362, 1989), hepatitis C virus (HCV) has become a focus of considerable medical research (Lauer, G. M and Walker, B. D., New Eng. J Med. 345, 41-52, 2001). HCV is a member of the Flaviviridae family of viruses in the *hepacivirus* genus, and is closely related to the *flavivirus* genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA in chimpanzee models of infection (Kolykhalov, A. A., Mihalik, K., Feinstone, S. M., and Rice, C. M. J. Virol. 74, 2046-2051, 2000). In addition to the NS3 serine protease, HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV). Following the initial acute infection, a majority of infected individuals develop chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology*, 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. *Hepatology*, 36, 5 Suppl. S30-S34, 2002).

The treatment of this chronic disease is an unmet clinical need, since current therapy is only partially effective and limited by undesirable side effects.

Current HCV therapies are based on (pegylated) interferon-alpha (IFN-α) in combination with ribavirin. This combination therapy yields a sustained virologic response in more than 40%0 of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective.

Thus, there is a high medical need for low molecular weight compounds that lead to an inhibition of HCV replication.

It has been surprisingly found that derivatives of pyrido[2,3-d]pyrimidines exhibit antiviral activity in mammals infected with HCV, in particular these derivatives inhibit HCV replication. These compounds are therefore useful in treating or combating HCV infections in mammals.

US2004/0038856 describes quinazoline derivatives that are inhibitors of TGFβ-R1 receptor kinase and TGF-β mediated signaling. WO00/12497 describes as well quinazoline derivatives that are inhibitors of TGF-β and/or p38-α kinase.

In addition, WO04/020584 describes compounds which are antagonists of chemokine receptor activity, and methods of making such compounds. Said patent publication also encompasses pharmaceutical compositions containing those compounds. Further methods are provided for the treatment of CCR4 chemokine receptor associated disorders and the treatment or prevention of asthma, rheumatoid arthritis, psoriasis, solid organ transplant rejection or chronic obstructive pulmonary disease.

WO2003059913 describes rho-kinase inhibitors, derivatives thereof, and the synthesis thereof. Said compounds are useful for inhibiting tumor growth, treating erectile dysfunction, and treating other indications mediated by Rho-kinase, e.g., coronary heart disease.

JP2003321472 discloses GRK inhibitors useful for the prevention and remedy of cardiac failure.

Furthermore, WO95/19774 describes bicyclic heteroaromatic compounds which inhibit the epidermal growth factor receptor and related receptors and, in particular, their tyrosine kinase enzymic activity. Said compounds are useful in suppressing tumors, especially breast cancers, where mitogenesis is heavily driven by EGFR family members. In addition, said compounds have utility as therapeutic agents against proliferative overgrowth diseases, including but not limited to, synovial pannus invasion in arthritis, vascular restenosis, psoriasis and angiogenesis. The compounds disclosed therein also are useful to treat pancreatitis and kidney disease and as a contraceptive agent.

U.S. Pat. No. 3,873,545 discloses substituted derivatives of pyrido[2,3d]pyrimidine, which are particularly useful as neuroleptic and tranquilizing agents.

Osselaere et al. (1973, 1974) describe pyrido[2,3-d]pyrimidine derivatives, in particular 4-amino-2-arylpyrido[2,3-d]pyrimidine derivatives having anti-inflammatory and spasmolytic properties.

After initial exposure to the Hepatitis C virus, HCV RNA can be detected in blood in 1-3 weeks. Within an average of 50 days virtually all patients develop liver cell injury. The majority of patients are asymptomatic and anicteric. Only 25-35 percent develop malaise, weakness, or anorexia, and some become icteric. Antibodies to HCV (anti-HCV) almost invariably become detectable during the course of illness. Anti-HCV can be detected in 50-70 percent of patients at the onset of symptoms and in approximately 90 percent of patients 3 months after onset of infection. HCV infection is self-limited in only 15 percent of cases. Recovery is characterized by disappearance of HCV RNA from blood and return of liver enzymes to normal.

About 85 percent of HCV-infected individuals fail to clear the virus by 6 months and develop chronic hepatitis with persistent, although sometimes intermittent, viremia. This capacity to produce chronic hepatitis is one of the most striking features of HCV infection. Chronic hepatitis C is typically an insidious process, progressing, if at all, at a slow rate without symptoms or physical signs in the majority of patients during the first two decades after infection. Symptoms first appear in many patients with chronic hepatitis C at the time of development of advanced liver disease.

In chronic hepatitis, inflammatory cells infiltrate the portal tracts and may also collect in small clusters in the parenchyma. The latter instance is usually accompanied by focal liver cell necrosis. The margin of the parenchyma and portal tracts may become inflamed, with liver cell necrosis at this site (interface hepatitis). If and when the disease progresses, the inflammation and liver cell death may lead to fibrosis. Mild fibrosis is confined to the portal tracts and immediately adjacent parenchyma. More severe fibrosis leads to bridging between portal tracts and between portal tracts and hepatic veins. Such fibrosis can progress to cirrhosis, defined as a state of diffuse fibrosis in which fibrous septae separate clusters of liver cells into nodules. The extent of fibrosis determines the stage of disease and can be reliably assessed. Severe fibrosis and necroinflammatory changes predict progression to cirrhosis. Once cirrhosis is established, complications can ensue that are secondary to liver failure and/or to portal hypertension, such as jaundice, ascites, variceal hemorrhage, and encephalopathy. The development of any of these complications marks the transition from a compensated to a decompensated cirrhosis.

Chronic hepatitis C infection leads to cirrhosis in at least 20 percent of patients within 2 decades of the onset of infection. Cirrhosis and end-stage liver disease may occasionally develop rapidly, especially among patients with concomitant alcohol use. Chronic infection by HCV is associated with an increased risk of liver cancer. The prevailing concept is that hepatocellular carcinoma (HCC) occurs against a background of inflammation and regeneration associated with chronic hepatitis over the course of approximately 3 or more decades. Most cases of HCV-related HCC occur in the presence of cirrhosis.

Liver fibrosis is one of the processes that occurs when the liver is damaged. Such damage may be the result of viral activity (e.g., chronic hepatitis types B or C) or other liver infections (e.g., parasites, bacteria); chemicals (e.g., pharmaceuticals, recreational drugs, excessive alcohol, exposure to pollutants); immune processes (e.g., autoimmune hepatitis); metabolic disorders (e.g., lipid, glycogen, or metal storage disorders); or cancer growth (primary or secondary liver cancer). Fibrosis is both a sign of liver damage and a potential contributor to liver failure via progressive cirrhosis of the liver.

It has been disclosed that the inhibition of the family TGFβ kinases is useful in the treatment of fibroproliferative disorders, including liver fibrosis. However, as it is noted above, liver fibrosis may be caused by different ethiological agents, including the Hepatitis C virus. Most importantly, liver fibrosis is a specific condition in the disease progression of patients infected with HCV.

It has been surprisingly found that the compounds of the present invention inhibit HCV replication. HCV replication refers to the process of reproducing or making copies of HCV RNA. In the present invention HCV replication both refers to the replication of the HCV virus as a whole or the replication of the HCV RNA genome.

It is important to treat HCV infected patients at early stages in order to avoid disease progression, thereby avoiding that the patient develops chronic hepatitis, liver fibrosis, cirrhosis, hepatocellular carcinoma (HCC), or death.

The compounds of the invention are valuable in that they may diminish the HCV viral load of a patient to undetected levels.

DISCLOSURE OF THE INVENTION

The present invention thus relates to the use of a compound of the formula (I) for the manufacture of a medicament useful for inhibiting HCV activity in a mammal infected with HCV. Said compound is a pyrido[2,3-d]pyrimidine of the formula (I):

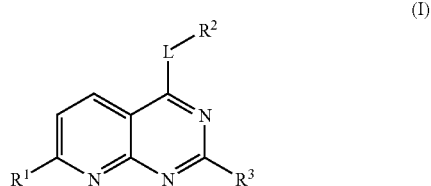

an N-oxide, salt, stereoisomeric form, racemic mixture, prodrug, ester or metabolite thereof, wherein $R^1$ is hydrogen, amino, mono- or disubstituted amino, wherein the substituent(s) of the amino may be selected from $C_{1-6}$alkyl, $C_{2-4}$alkenyl, $C_{2-6}$alkynyl, $C_{1-4}$alkyloxy$C_{1-4}$alkyl, di$C_{1-4}$alkylamino$C_{1-4}$ alkyl piperidin-1-yl-$C_{1-4}$alkyl, aryl$C_{1-4}$alkyl, wherein the aryl group may be further substituted with $C_{1-4}$alkyl, or $C_{1-4}$alkoxy;

L is —$NR^8$—, —$NR^8$—$C_{1-6}$alkanediyl-, —$NR^8$—CO—$C_{1-6}$alkanediyl-, —$NR^8$—$SO_2$—$C_{1-6}$alkanediyl-, —O—, —O—$C_{1-6}$alkanediyl-, —O—CO—, —O—CO—$C_{1-6}$alkanediyl-, —S—, —S—$C_{1-6}$alkanediyl-, or

wherein the dotted ring together with N and Z form a $Het^1$ cycle having 5 to 8 members including ring members N and Z, and wherein said L ring is attached to the pyrido[2,3-d]pyrimidine ring by the nitrogen atom;

Z represents N or CH;

$R^2$ represents hydrogen, hydroxy$C_{1-6}$alkyl, $C_{3-7}$cycloalkyl, aryl, Het$^1$, or Het$^2$, wherein said $C_{3-7}$cycloalkyl, aryl Het$^1$ and Het$^2$ are each independently optionally substituted with one or more substituents selected from $C_{1-4}$alkyl, $C_{2-4}$alkenyl, $C_{2-6}$alkynyl polyhalo$C_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, NR$^{4a}$R$^{4b}$, NR$^{4a}$COR$^6$, NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, —SO$_2$NR$^{4a}$R$^{4b}$, morpholin-4-yl, phenyl, aminophenyl, and aminophenylcarbonyl, and wherein the $C_{1-4}$alkyl may be further substituted with —COOR$^7$;

$R^3$ represents $C_{1-6}$alkyl, $C_{3-7}$cycloalkyl, aryl, aryl$C_{1-6}$alkyl, Het$^1$, Het$^2$ or Het$^2C_{1-6}$alkyl each independently optionally substituted with one or more substituents selected from $C_{1-4}$alkyl $C_{2-4}$alkenyl, $C_{2-4}$alkynyl polyhalo$C_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$COOR$^7$, NR$^{4a}$CONR$^{4a}$R$^{4b}$, NR$^{4a}$SOR$^5$, NR$^{4a}$SO$_2$R$^5$, —SR$^5$, —SOR$^7$, —SO$_2$R$^5$, —SO$_3$R$^7$, and —SO$_2$NR$^{4a}$R$^{4b}$;

each $R^{4a}$ and $R^{4b}$ is independently hydrogen, $C_{1-4}$alkyl, hydroxy$C_{1-4}$alkyl, Het$^1C_{1-4}$alkyl, polyhalo$C_{1-4}$alkyl, cyano, or nitro;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl; and each $R^8$ is independently hydrogen, $C_{1-10}$alkyl, $C_{2-10}$alkenyl, $C_{2-10}$alkynyl, $C_{1-10}$alkylcarbonyl, amino$C_{1-10}$alkyl, aryl, arylcarbonyl, aryl $C_{1-10}$alkyl, Het$^1$, Het$^1C_{1-6}$alkyl, or a nitrogen-protecting group, wherein the aryl is optionally substituted with 1 to 3 substituents selected from $C_{1-4}$alkyl, $C_{2-4}$alkenyl, $C_{2-4}$alkynyl, $C_{1-4}$alkylcarbonyl, phenyl, $C_{1-4}$alkylphenyl, phenylcarbonyl, aminophenyl, amino$C_{1-4}$ alkylphenyl, aminophenylcarbonyl, halo, —OR$^6$, —NR$^{4a}$R$^{4b}$, —SR$^5$, —SOR$^5$, —NR$^{4a}$SOR$^5$, —NR$^{4a}$SO$_2$R$^5$, —SO$_2$R$^5$, —OCOR$^6$, —NR$^{4a}$COR$^6$, —NR$^{4a}$CONR$^{4a}$R$^{4b}$, —NR$^{4a}$COOR$^6$, —OCONR$^{4a}$R$^{4b}$, —COOR$^6$, —SO$_3$R$^6$, —CONR$^{4a}$R$^{4b}$, —SO$_2$NR$^{4a}$R$^{4b}$, cyano, polyhalo$C_{1-4}$alkyl, and nitro;

Het$^1$ as a group or part of a group is defined as a saturated or partially unsaturated monocyclic, bicyclic or tricyclic heterocycle having preferably 3 to 12 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halo, hydroxy, oxo, optionally mono- or disubstituted amino, nitro, cyano, polyhalo$C_{1-4}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are hydrogen, or $C_{1-4}$alkyl;

Het$^2$ as a group or part of a group is defined as an aromatic monocyclic, bicyclic or tricyclic heterocycle having 3 to 14 ring members, preferably 5 to 10 ring members and more preferably 5 to 6 ring members, which contains one or more heteroatom ring members each independently selected from nitrogen, oxygen or sulfur, and which is optionally substituted on one or more carbon atoms by $C_{1-6}$alkyl, optionally mono- or disubstituted amino$C_{1-6}$alkyl, hydroxy$C_{1-6}$alkyl, $C_{1-6}$alkyloxy, halo, hydroxy, optionally mono- or disubstituted amino, nitro, cyano, polyhalo-$C_{1-4}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are hydrogen, or $C_{1-4}$alkyl; and aryl as a group or part of a group is phenyl.

In an embodiment, the present invention relates to the use of a compound of the formula (II) for the manufacture of a medicament useful for inhibiting HCV activity in a mammal infected with HCV,

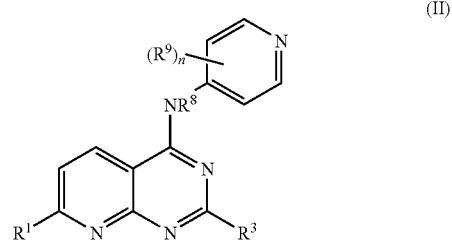

(II)

an N-oxide, salt, stereoisomeric form, racemic mixture, prodrug, ester or metabolite thereof, wherein $R^1$, $R^3$, and $R^8$ are as defined above, $R^9$ represents $C_{1-4}$alkyl, $C_{2-4}$alkenyl, $C_{2-4}$alkynyl, polyhalo$C_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, NR$^{4a}$R$^{4b}$, —NR$^{4a}$COR$^6$, —NR$^{4a}$CONR$^{4a}$R$^{4b}$, —NR$^{4a}$SOR$^5$—NR$^{4a}$SO$_2$R$^5$, —SR$^5$, —SOR$^7$, —SO$_2$R$^5$, —SO$_3$R$^7$, —SO$_2$NR$^{4a}$R$^{4b}$, morpholin-4-yl, phenyl, aminophenyl, or aminophenyl-carbonyl, and wherein the $C_{1-4}$alkyl may be further substituted with —COOR$^7$; and n is 0, 1, 2, 3, or 4.

In an embodiment, the present invention relates to the use of a compound of the formula (III) for the manufacture of a medicament useful for inhibiting HCV activity in a mammal infected with HCV,

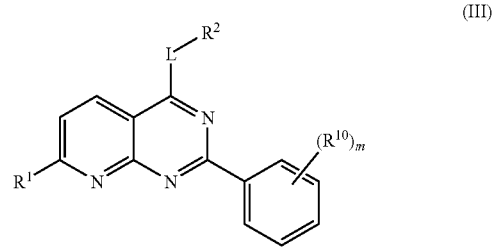

(III)

an N-oxide, salt, stereoisomeric form, racemic mixture, prodrug, ester or metabolite thereof, wherein $R^1$, L, and $R^2$ are as defined above, and $R^{10}$ represents $C_{1-4}$alkyl $C_{2-4}$alkenyl, $C_{2-4}$alkynyl, polyhalo$C_{1-4}$alkyl, halo, cyano, nitro, —COR$^6$, —COOR$^7$, CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$COOR$^7$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, and —SO$_2$NR$^{4a}$R$^{4b}$; and m is 0, 1, 2, 3, or 4.

In an embodiment, the present invention relates to the use of a compound of the formula (IV) for the manufacture of a medicament useful for inhibiting HCV activity in a mammal infected with HCV,

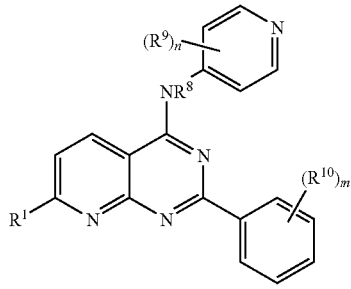

(IV)

an N-oxide, salt, stereoisomeric form, racemic mixture, prodrug, ester and metabolite thereof, wherein $R^1$, $R^8$, $R^9$, $R^{10}$, m and n are as defined above.

In an embodiment, the present invention relates to the use of a compound of the formula (V) for the manufacture of a medicament useful for inhibiting HCV activity in a mammal infected with HCV,

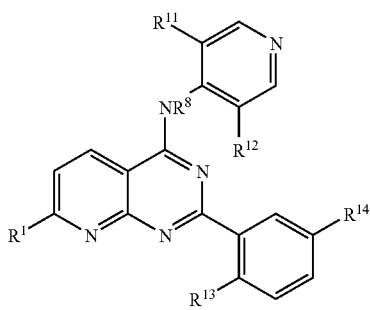

(V)

an N-oxide, salt, stereoisomeric form, racemic mixture, prodrug, ester and metabolite thereof, wherein $R^1$, and $R^8$ are as defined above;

each $R^{11}$ and $R^{12}$ represent, independently, hydrogen, $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, $OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, or aminophenylcarbonyl, and wherein the $C_{1-4}$alkyl may be further substituted with —$COOR^7$;

$R^{13}$ represents hydrogen, or halo; and $R^{14}$ represents halo.

In an embodiment, the present invention relates to the use of a compound of the formula (V) for the manufacture of a medicament for inhibiting HCV replication in a mammal infected with HCV. Said compound is a pyrido[2,3-d]pyrimidine of the formula (V):

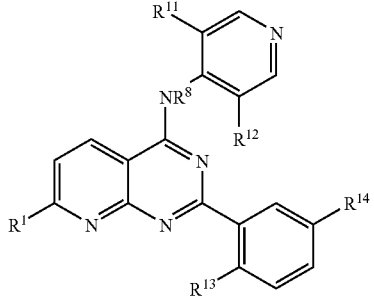

(V)

a salt, stereoisomeric form, or racemic mixture thereof, wherein $R^1$ is hydrogen, amino, mono- or disubstituted amino, wherein the substituents of the amino may be selected from $C_{1-6}$alkyl, $C_{1-4}$alkyloxy$C_{1-4}$alkyl, di$C_{1-4}$alkylamino-$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$ and $R^{4b}$ is independently hydrogen, or $C_{1-4}$alkyl;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, polyhalo$C_{1-4}$alkyl, halo, —$COR^6$, —$COOR^7$, —$OR^7$, —$NR^{4a}R^{4b}$, —$NR^{4a}SO_2R^5$, —$SR^5$, —$SO_2R^5$, or —$SO_2NR^{4a}R^{4b}$;

$R^{13}$ represents hydrogen, or halo; and $R^{14}$ represents halo.

In a further aspect the invention relates to a method of inhibiting HCV replication in a mammal infected with HCV, said method comprising the administration of an HCV inhibitory effective amount of a compound of formulae (I), (II), (III), (IV), or (V) as specified above or as further specified hereinafter.

In a further aspect the invention relates to a method of treating a mammal infected with HCV, said method comprising the administration of an HCV inhibitory effective amount of a compound of formulae (I), (II), (III), (IV), or (V) as specified above or as further specified hereinafter.

A further embodiment of the invention relates to the use of the compounds of the formula (V) for the manufacture of a medicament for inhibiting HCV replication in a mammal infected with HCV. Said compounds are pteridines of the formula (V) and the salts, stereoisomeric forms, or racemic mixtures thereof, wherein $R^1$ is hydrogen, amino, mono- or disubstituted amino, wherein the substituents of the amino may be selected from $C_{1-6}$alkyl, $C_{1-4}$alkyloxy$C_{1-4}$alkyl, di$C_{1-4}$alkylamino-$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, polyhalo$C_{1-4}$alkyl, halo, —$COR^6$, —$COOR^7$, —$OR^7$, —$SR^5$;

$R^{13}$ represents hydrogen, or halo; and $R^{14}$ represents halo.

Thus, further embodiments of the invention relate to the method of inhibiting HCV replication in a mammal infected with HCV, and to the method of treating a mammal infected with HCV, said methods comprising the administration of an HCV inhibitory effective amount of a compound of formula (V) wherein $R^1$, $R^8$, $R^{11}$, $R^{12}$, $R^{13}$, $R^{14}$ are as defined in the previous paragraph.

A further embodiment of the invention relates to the use of the compounds of the formula (V) for the manufacture of a medicament for inhibiting HCV replication in a mammal infected with HCV. Said compounds are pteridines of the formula (V) and the salts, stereoisomeric forms, or racemic mixtures thereof, wherein $R^1$ is hydrogen, amino, monosubstituted amino, wherein the substituents of the amino may be selected from $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkoxy;

each $R^5$ is $C_{1-4}$alkyl;
each $R^7$ is $C_{1-4}$alkyl;
$R^8$ is hydrogen, or a nitrogen-protecting group;
each $R^{11}$ and $R^{12}$ represent, independently, hydrogen, $C_{1-4}$alkyl which may be further substituted with —COOR$^7$, polyhalo$C_{1-4}$alkyl, halo, —COOR$^7$, —OR$^7$, —SR$^5$;
$R^{13}$ represents hydrogen, or halo; and
$R^{14}$ represents halo.

Thus, further embodiments of the invention relate to the method of inhibiting HCV replication in a mammal infected with HCV, and to the method of treating a mammal infected with HCV, said methods comprising the administration of an HCV inhibitory effective amount of a compound of formula (V) wherein $R^1$, $R^8$, $R^{11}$, $R^{12}$, $R^{13}$, $R^{14}$ are as defined in the previous paragraph.

A further embodiment of the invention relates to the use of the compounds of the formula (V) for the manufacture of a medicament for inhibiting HCV replication in a mammal infected with HCV. Said compounds are pteridines of the formula (V) and the salts, stereoisomeric forms, or racemic mixtures thereof, wherein $R^1$ is hydrogen, amino, monosubstituted amino, wherein the substituents of the amino may be selected from $C_{1-4}$alkyloxy$C_{1-4}$alkyl, piperidin-1-yl-$C_{1-4}$alkyl, phenyl$C_{1-6}$alkyl, wherein the phenyl group may be further substituted with $C_{1-4}$alkoxy;

each $R^5$ is $C_{1-4}$alkyl;
$R^8$ is hydrogen, or a nitrogen-protecting group;
each $R^{11}$ and $R^{12}$ represent, independently, hydrogen, $C_{1-4}$alkyl which may be further substituted with —COOR$^7$, halo, —OR$^7$, or —SR$^5$;
$R^{13}$ represents hydrogen, or halo; and
$R^{14}$ represents halo.

Thus, further embodiments of the invention relate to the method of inhibiting HCV replication in a mammal infected with HCV, and to the method of treating a mammal infected with HCV, said methods comprising the administration of an HCV inhibitory effective amount of a compound of formula (V) wherein $R^1$, $R^8$, $R^{11}$, $R^{12}$, $R^{13}$, $R^{14}$ are as defined in the previous paragraph.

A further embodiment of the invention relates to the use of the compounds of the formula (V) for the manufacture of a medicament for inhibiting HCV replication in a mammal infected with HCV. Said compounds are pteridines of the formula (V) and the salts, stereoisomeric forms, or racemic mixtures thereof, wherein $R^1$ is hydrogen, or amino;
each $R^5$ is $C_{1-4}$alkyl;
$R^8$ is hydrogen, or a nitrogen-protecting group;
each $R^{11}$ and $R^{12}$ represent, independently, hydrogen, $C_{1-4}$alkyl, —OR$^7$, or —SR$^5$;
$R^{13}$ represents hydrogen, or halo; and
$R^{14}$ represents halo.

Thus, further embodiments of the invention relate to the method of inhibiting HCV replication in a mammal infected with HCV, and to the method of treating a mammal infected with HCV, said methods comprising the administration of an HCV inhibitory effective amount of a compound of formula (V) wherein $R^1$, $R^8$, $R^{11}$, $R^{12}$, $R^{13}$, $R^{14}$ are as defined in the previous paragraph.

A method of treating clinical conditions relating to HCV infection in a mammal, said method comprising the administration of an HCV inhibitory effective amount of a compound of formula (V) wherein $R^1$, $R^8$, $R^{11}$, $R^{12}$, $R^{13}$, $R^{14}$ are as defined hereinafter.

A method as in the previous paragraph wherein the clinical conditions are other than liver fibrosis.

The compounds of formulae (I), (II), (III), (IV), and (V) show activity against the HCV virus and are therefore useful as a medicament, and in the manufacture of a medicament for preventing, treating or combating infection or disease associated with HCV infection.

The compounds of formulae (I), (II), (III), (IV), and (V) show activity against the HCV virus and are therefore useful as a medicament, and in the manufacture of a medicament for preventing, treating or combating clinical conditions associated with HCV infection other than liver fibrosis.

The term "$C_{1-2}$alkyl" as a group or part of a group defines straight and branched chained saturated hydrocarbon radicals having from 1 to 2 carbon atoms, such as, for example, methyl, ethyl, and the like.

The term "$C_{1-4}$alkyl" as a group or part of a group defines straight and branched chained saturated hydrocarbon radicals having from 1 to 4 carbon atoms, such as, for example, the groups defined for $C_{1-2}$alkyl and propyl, butyl, 2-methylpropyl and the like.

The term "$C_{1-6}$alkyl" as a group or part of a group defines straight and branched chained saturated hydrocarbon radicals having from 1 to 6 carbon atoms such as, for example, the groups defined for $C_{1-4}$alkyl and pentyl, hexyl, 2-methylbutyl, 3-methylpentyl and the like.

The term "$C_{1-10}$alkyl" as a group or part of a group defines straight and branched chained saturated hydrocarbon radicals having from 1 to 10 carbon atoms such as, for example, the groups defined for $C_{1-6}$alkyl and heptyl, octyl, nonyl, decyl and the like.

The term "$C_{2-4}$alkenyl" as a group or part of a group defines straight and branched chained hydrocarbon radicals having saturated carbon-carbon bonds and at least one double bond, and having from 2 to 4 carbon atoms, such as, for example, ethenyl, prop-1-enyl, but-1-enyl, but-2-enyl, and the like. Preferred are $C_{2-4}$alkenyls having one double bond.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, the groups defined for $C_{2-4}$alkenyl and pent-1-enyl, pent-2-enyl, hex-1-enyl, hex-2-enyl, hex-3-enyl, 1-methyl-pent-2-enyl and the like. Preferred are $C_{2-6}$alkenyls having one double bond.

The term "$C_{2-10}$alkenyl" as a group or part of a group defines straight and branched chained hydrocarbon radicals having saturated carbon-carbon bonds and at least one double bond, and having from 2 to 10 carbon atoms, such as, for example, the groups defined for $C_{2-6}$alkenyl and hept-1-enyl, hept-2-enyl, 2-methyl-hept-1-enyl, oct-3-enyl, non-4-enyl, 1-methyl-non-2-enyl and the like. Preferred are $C_{2-10}$alkenyls having one double bond.

The term "$C_{2-4}$alkynyl" as a group or part of a group defines straight and branched chained hydrocarbon radicals having saturated carbon-carbon bonds and at least one triple bond, and having from 2 to 4 carbon atoms, such as, for example, ethynyl, prop-1-ynyl, but-1-ynyl, but-2-ynyl, and the like. Preferred are $C_{2-4}$alkynyls having one triple bond.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, the groups defined for $C_{2-4}$alkynyl and pent-1-ynyl, pent-2-ynyl, hex-1-ynyl, hex-2-ynyl, hex-3-ynyl, 1-methyl-pent-2-ynyl, pent-2-en-4-ynyl and the like. Preferred are $C_{2-6}$alkynyls having one triple bond.

The term "$C_{2-10}$alkynyl" as a group or part of a group defines straight and branched chained hydrocarbon radicals having saturated carbon-carbon bonds and at least one triple bond, and having from 2 to 10 carbon atoms, such as, for example, the groups defined for $C_{2-6}$alkynyl and hept-1-ynyl, hept-2-ynyl, 2-methyl-hept-1-ynyl, oct-3-ynyl, non-4-ynyl, 1-methyl-non-2-ynyl and the like. Preferred are $C_{2-10}$alkynyls having one triple bond.

The term "$C_{1-6}$alkanediyl" as a group or part of a group defines bivalent straight and branched chained hydrocarbons having from 1 to 6 carbon atoms such as, for example, methanediyl, 1,2-ethanediyl, or 1,1-ethanediyl, 1,3-propanediyl, 1,3-butanediyl, 1,4-butanediyl, 1,3-pentanediyl, 1,5-pentanediyl, 1,4-hexanediyl, 1,6-hexanediyl, and the like.

The term "$C_{3-7}$cycloalkyl" is generic to cyclopropyl, cyclobutyl, cyclopentyl, cyclohexyl and cycloheptyl.

The term "aryl" as a group or part of a group is meant to include phenyl or naphtyl. In a preferred embodiment, the term "aryl" as a group or part of a group is phenyl.

The term "halo" is generic to fluoro, chloro, bromo or iodo.

As used in the foregoing and hereinafter "polyhalo$C_{1-4}$alkyl" as a group or part of a group is defined as mono- or polyhalosubstituted $C_{1-4}$alkyl, for example, 1,1,1-trifluoroethyl, 1,1-difluoro-ethyl, the polyhalomethyl groups mentioned hereinafter, and the like. A preferred subgroup of polyhalo$C_{1-4}$alkyl is polyhalomethyl, wherein the latter as a group or part of a group is defined as mono- or polyhalo-substituted methyl, in particular methyl with one or more fluoro atoms, for example, difluoromethyl or trifluoromethyl. In case more than one halogen atom is attached to an alkyl group within the definition of polyhalomethyl or polyhalo$C_{1-4}$alkyl, they may be the same or different.

The term "nitrogen-protecting group" refers to an amino-protecting group such as such as $C_{1-10}$alkoxy-carbonyl, aryl$C_{1-10}$alkoxy-carbonyl, like benzoyl, anisoyl-, isobutyroyl-, acetyl-, or tert-butylbenzoyl (Breipohl et al. (1997) Tetrahedron 53, 14671-14686). The nitrogen-protecting group may be as well an acid-labile nitrogen-protecting group such as dimethoxytrityl. In one embodiment, the nitrogen-protecting group is selected from $C_{1-6}$alkyloxycarbonyl, arylmethoxycarbonyl, trifluoroacetyl, and arylmethyl. In another embodiment, the nitrogen-protecting group is t-butoxycarbonyl, benzyloxycarbonyl, benzyl, or trifluoromethyl.

It should also be noted that the radical positions on any molecular moiety used in the definitions, unless indicated otherwise, may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

The N-oxide forms of the present compounds are meant to comprise any one of the compounds of the present invention wherein one or several nitrogen atoms are oxidized to the so-called N-oxide.

For therapeutic use, the salts of the compounds of the present invention are those wherein the counter-ion is pharmaceutically or physiologically acceptable. However, salts having a pharmaceutically unacceptable counter-ion may also find use, for example, in the preparation or purification of a pharmaceutically acceptable compound of formulae (I), (II), (III), (IV), or (V). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecyl-sulphuric, heptanoic, hexanoic, benzoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, toluenesulfonic, cyclamic, salicylic, p-amino-salicylic, pamoic and the like acids.

Conversely said acid addition salt forms can be converted by treatment with an appropriate base into the free base form.

The compounds of formulae (I), (II), (III), (I), or (V) containing an acidic proton may also be converted into their non-toxic metal or amine addition base salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Alternatively, when a carboxyl moiety is present on the compound of formulae (I), (II), (III), (IV), or (V), the compound may also be supplied as a salt with a pharmaceutically acceptable cation.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

In the event that any of the substituents of formulae (I), (II), (III), (IV), or (V) contain chiral centers, as some, indeed, do, the compounds of formulae (I), (II), (III), (I), or (V) include all stereoisomeric forms thereof, both as isolated stereoisomers and mixtures of these stereoisomeric forms.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formulae (I), (II), (III), (IV), or (V) can be obtained separately by conventional methods. Appropriate physical separation methods that may advantageously be employed are, for example, selective crystallization and chromatography, e.g. column chromatography.

The present compounds may also exist in their tautomeric forms. Such forms, although not explicitly indicated in the above formula are intended to be included within the scope of the present invention. For example, within the definition of Het², for example an 1,2,4-oxadiazole may be substituted with a hydroxy or a mercapto group in the 5-position, thus being in equilibrium with its respective tautomeric form as depicted below.

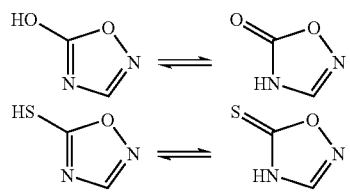

The term "prodrug" as used throughout this text means the pharmacologically acceptable derivatives such as esters, amides and phosphates, such that the resulting in vivo biotransformation product of the derivative is the active drug as defined in the compounds of formulae (I), (II), (III), (IV), or (V). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either by routine manipulation or in vivo, to the parent compound. For example, a substituent containing sulfhydryl could be coupled to a carrier which renders the compound biologically inactive until removed by endogenous enzymes or, for example, by enzymes targeted to a particular receptor or location in the subject.

Prodrugs are characterized by excellent aqueous solubility, increased bioavailability and are readily metabolized into the active inhibitors in vivo.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", "compounds of formula (II)", "compounds of formula (III)", "compounds of formula (IV)", "compounds of formula (V)", or "the present compounds" or similar term is meant to include the compounds of general formulae (I), (II), (III), (IV), or (V), their N-oxides, salts, stereoisomeric forms, racemic mixtures, prodrugs, esters and metabolites, as well as their quaternized nitrogen analogues. An interesting subgroup of the compounds of the present invention or any subgroup thereof are the N-oxides, salts and all the stereoisomeric forms thereof.

Embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein the 4-pyridyl forms a N-oxide, for example the N-oxide of compound nr. 21.

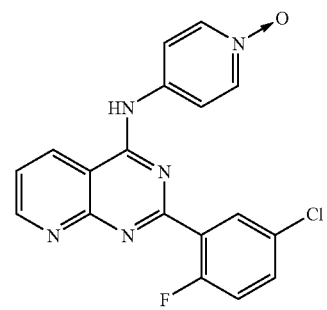

N-oxide of compound nr. 21

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein the compound of formulae (I), (II), (III), (IV), or (V) occur as an acid-addition salt, wherein the salt preferably is selected from hydrochloride, hydrobromide, trifluoroacetate, fumarate, chloroacetate, methanesulfonate, oxalate, acetate and citrate.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen, amino, mono- or disubstituted amino, wherein the substituent(s) of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl phenyl$C_{1-6}$alkyl wherein the phenyl group may be further substituted with $C_{1-4}$alkyl, or $C_{1-4}$alkoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen, amino, mono- or disubstituted amino, wherein the substituent(s) of the amino may be selected from $C_{1-4}$alkyl, $C_{1-4}$alkyloxy$C_{1-4}$alkyl, di$C_{1-4}$alkylamino$C_{1-4}$alkyl, piperidin-1-yl-$C_{1-4}$alkyl phenyl$C_{1-6}$alkyl, wherein the phenyl group may be further substituted with $C_{1-4}$alkoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen, amino, mono- or disubstituted amino, wherein the substituent(s) of the amino may be selected from $C_{1-2}$alkyl, $C_{1-2}$alkyloxy$C_{1-2}$alkyl, di$C_{1-2}$alkylamino$C_{1-2}$alkyl, piperidin-1-yl-$C_{1-2}$alkyl, phenyl$C_{1-2}$alkyl, wherein the phenyl group may be further substituted with $C_{1-2}$alkoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen, amino, mono- or disubstituted amino, wherein the substituent(s) of the amino may be selected from methyl, methyloxyethyl, dimethylaminoethyl, piperidin-1-yl-ethyl, phenylmethyl, wherein the phenyl group may be further substituted with methoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen, amino, or monosubstituted amino, wherein the substituent of the amino may be selected from methyloxyethyl, dimethylaminoethyl, piperidin-1-yl-ethyl, and phenylmethyl, wherein the phenyl group is further substituted with methoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is independently hydrogen or amino.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^1$ is amino, or mono- or disubstituted amino, wherein the substituent(s) of the amino may be selected from $C_{1-6}$alkyl, $C_{1-4}$alkyloxy-$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^8$ is hydrogen, $C_{1-10}$alkyl, amino$C_{1-10}$alkyl, phenyl$C_{1-10}$alkyl, Het$^1C_{1-6}$alkyl, or a nitrogen-protecting group, wherein the phenyl is optionally substituted with 1 to 3 substituents selected from $C_{1-4}$alkyl, $C_{1-4}$alkyl-carbonyl, halo, —OR$^6$, NR$^{4a}$R$^{4b}$, —SR$^5$, and polyhalo-$C_{1-4}$alkyl.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^8$ is hydrogen, $C_{1-6}$alkyl, amino$C_{1-6}$alkyl, phenyl$C_{1-6}$alkyl, Het$^1C_{1-6}$alkyl, or $C_{1-6}$alkoxy-carbonyl.

Further embodiments of the present invention are those compounds of formulae (I), (II), (III), (IV), or (V), any of the subgroups of compounds of formulae (I), (II), (III), (IV), or (V), or the use of said compounds for the manufacture of a medicament useful for inhibiting HCV activity, wherein $R^8$ is hydrogen, $C_{1-6}$alkyl, amino$C_{1-4}$alkyl, phenyl$C_{1-4}$alkyl pyrrolidin-1-yl-$C_{1-4}$alkyl, or $C_{1-6}$alkoxycarbonyl.

Further embodiments of the present invention are those compounds of formula (V), any of the subgroups of compounds of formula (V), or the use of said compounds for the manufacture of a medicament useful for inhibiting HCV activity, wherein each $R^{11}$ and $R^{12}$ represent, independently, hydrogen, $C_{1-4}$alkyl, polyhalo$C_{1-4}$alkyl halo, —COR$^6$, —COOR$^7$, —OR$^7$, —NR$^{4a}$R$^{4b}$, or —SR$^5$, and wherein the $C_{1-4}$alkyl may be further substituted with —COOR$^7$.

Further embodiments of the present invention are those compounds of formula (V), any of the subgroups of compounds of formula (V), or the use of said compounds for the manufacture of a medicament useful for inhibiting HCV activity, wherein each $R^{11}$ and $R^{12}$ represent, independently, hydrogen, methyl, trifluoromethyl, halo, —COR$^6$, —COOR$^7$, —OR$^7$, or —SR$^5$, and wherein the methyl may be further substituted with —COOR$^7$.

Further embodiments of the present invention are those compounds of formula (V), any of the subgroups of compounds of formula (V), or the use of said compounds for the manufacture of a medicament useful for inhibiting HCV activity, wherein $R^{13}$ represents hydrogen or fluoro.

Further embodiments of the present invention are those compounds of formula (V), any of the subgroups of compounds of formula (V), or the use of said compounds for the manufacture of a medicament useful for inhibiting HCV activity, wherein $R^{14}$ represents chloro, bromo, or fluoro.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein $R^1$ is independently hydrogen, amino, mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

$R^{4a}$, $R^{4b}$, $R^5$, $R^6$, $R^7$ are as defined above for the compounds of formula (V);

$R^8$ is hydrogen, or a nitrogen-protecting group;

each $R^{11}$ and $R^{12}$ represent, independently, hydrogen, $C_{1-4}$alkyl polyhalo$C_{1-4}$alkyl, halo, —COR$^6$, —COR$^7$, —OR$^7$, —NR$^{4a}$R$^{4b}$, —NR$^{4a}$SO$_2$R$^5$, —SR$^5$, —SO$_2$R$^5$, or —SO$_2$NR$^{4a}$R$^{4b}$;

$R^{13}$ represents hydrogen, or halo;
$R^{14}$ represents halo;
with the proviso that the following two compounds are excluded:
2-(5-chloro-2-fluorophenyl)-N-4-pyridinyl-pyrido[2,3-d]pyrimidin-4-amine;
2-(5-chloro-2-fluorophenyl)-N-(3-methyl-4-pyridinyl)-pyrido[2,3-d]pyrimidin-4-amine.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein
$R^1$ is amino, or mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;
each $R^{4a}$ and $R^{4b}$ is independently hydrogen, or $C_{1-4}$alkyl;
each $R^5$ is independently hydrogen, or $C_{1-4}$alkyl;
each $R^6$ is independently hydrogen, or $C_{1-4}$alkyl;
each $R^7$ is independently hydrogen, or $C_{1-4}$alkyl;
$R^8$ is hydrogen, or a nitrogen-protecting group;
each $R^{11}$ and $R^{12}$ represent, independently, hydrogen, $C_{1-4}$alkyl which may be further substituted with —COOR$^7$, polyhalo$C_{1-4}$alkyl, halo, —COR$^6$, —COOR$^7$, —OR$^7$, —NR$^{4a}$R$^{4b}$, —NR$^{4a}$SO$_2$R$^5$, —SR$^5$, —SO$_2$R$^5$, or —SO$_2$NR$^{4a}$R$^{4b}$;
$R^{13}$ represents hydrogen, or halo; and
$R^{14}$ represents halo.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein
$R^1$ is amino, or mono- or disubstituted amino, wherein the substituents of the amino may be selected from $C_{1-6}$alkyl, $C_{1-4}$alkyloxy$C_{1-4}$alkyl di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;
each $R^{4a}$, $R^{4b}$, $R^5$, $R^7$, independently, are hydrogen, or $C_{1-4}$alkyl;
$R^8$ is hydrogen, or a nitrogen-protecting group;
each $R^{11}$ and $R^{12}$ represent, independently, hydrogen, $C_{1-4}$alkyl, halo, —OR$^7$, or —SR$^5$;
$R^{13}$ represents hydrogen, or halo; and
$R^{14}$ represents halo.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein
$R^1$ is amino;
each $R^{4a}$, $R^{4b}$, $R^5$, $R^7$, independently, are hydrogen, or $C_{1-4}$alkyl;
$R^8$ is hydrogen, or a nitrogen-protecting group;
each $R^{11}$ and $R^{12}$ represent, independently, hydrogen, $C_{1-4}$alkyl, halo, —OR$^7$, or —SR$^5$;
$R^{13}$ represents hydrogen, or halo; and
$R^{14}$ represents halo.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein
$R^{11}$ is hydrogen; and
$R^{12}$ is $C_{1-4}$alkyl, halo, $C_{1-4}$alkoxy, $C_{1-4}$alkylthio, or trifluoromethyl.

Further embodiments of the present invention are those compounds of formula (V), any of the subgroups of compounds of formula (V), or the use of said compounds for the manufacture of a medicament useful for inhibiting HCV activity, and the N-oxides, salts, stereoisomeric forms, racemic mixtures, prodrugs, esters and metabolites thereof, wherein
$R^{13}$ and $R^{14}$ represents halo.

Compounds of particular interest are those compounds of formula (I) listed in Table 1 below, in particular compounds number 1, number 2, number 3, number 6, number 7, number 8, number 9, number 10, number 11, number 22, and number 26, and its N-oxides, salts and stereoisomers.

A number of synthetic routes may be employed to produce the compounds of the invention. In general, they may be synthesized using reactions known in the art. Any art-known method for synthesis may be employed. However, the following synthetic routes are convenient for preparation of the invention compounds.

The compounds of the formula (V) may be synthesized following a procedure adapted from Wamhoff, H.; Kroth, E. *Synthesis*, 1994, 405-410 as described in Scheme 1.

Scheme 1

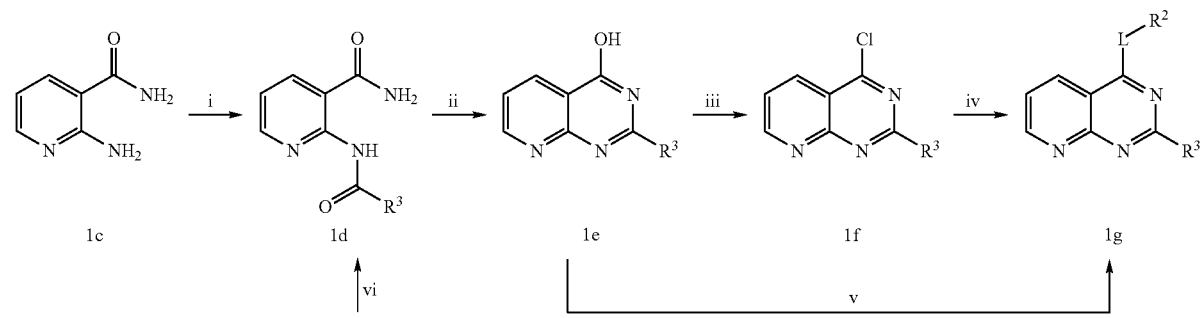

-continued

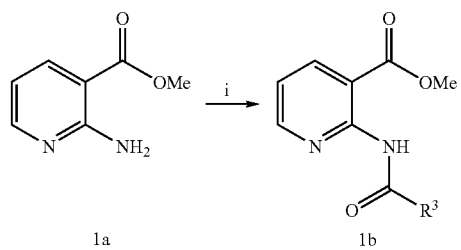

Basically, a methyl 2-amino-3-pyridinecarboxylate (1a) is reacted with acylchloride in the presence of a suitable solvent such as chloroform or pyridine to afford 2-acylaminopyridin-3-carboxylates (1b). Said 2-acylaminopyridin-3-carboxylates (1b) are converted with for example ammonium hydroxide into 2-acylaminopyridin-3-amides (1d). Optionally, 2-acylaminopyridin-3-amides (1d) may already be obtained by acylation of a 2-amino-3-pyridineamide (1c).

The 2-acylaminopyridin-3-amides (1d) are then cyclized by the addition of a base to form pyrido[2,3-d]pyrimidin-4-ol derivates of formula (1e). The alcohol may then be replaced by a halogen with the help of a halogenating agent such as thionyl chloride in a suitable solvent like chloroform, dichloroethane or tetrahydrofuran (THF) in presence of a catalytic amount of dimethylformamide (DMF). Following, a nucleophilic substitution is performed on compound (1f) with an amine or an alcohol of formula $HLR^2$, together with a suitable base, such as TEA or DIPEA in an organic solvent such as DCM, THF or DMF, yielding compound (1g).

Alternatively, the 2-acylaminopyridin-3-amides may be converted in a one-pot procedure into the pyrido[2,3-d]pyrimidines of formula (V) by reacting compound of formula (1e) with an amine or alcohol of the formula $HLR^2$ together with a suitable base, such as TEA or DIPEA in the presence of benzotriazole-1-yl-oxy-tris-pyrrolidino-phosphonium hexafluorophosphate (PyBOP). In the formula $HLR^2$, H is hydrogen, and L and $R^2$ have the meanings indicated above in the definition of the substituents of compound of formula (V).

Scheme 2

Alternatively, the compounds of the formula (V) can be prepared from the corresponding pyridopyrimidinone derivates as starting materials followed by their conversion to the iminochlorides and the subsequent displacement of the chlorine atom with an appropriate amine such as a 4-aminopyridine as shown below in Scheme 2.

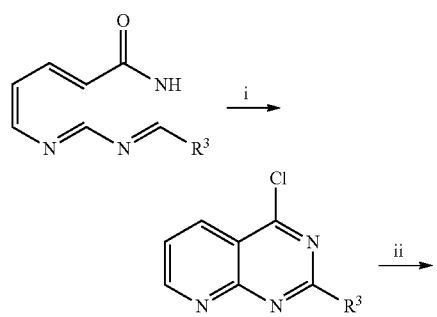

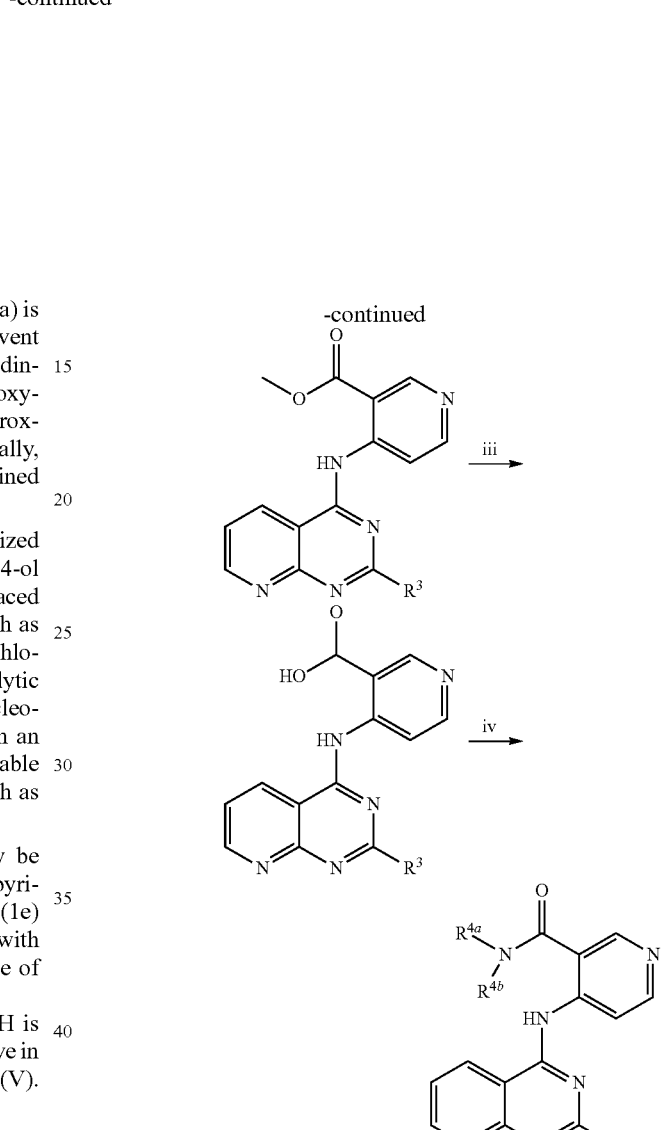

(i) thionyl chloride, DMF;
(ii) 4-aminonicotinic acid methyl ester, TEA;
(iii) NaOH;
(iv) PyBOP, TEA, $HNR^{4a}R^{4b}$.

Schemes 3 and 4, shown below, provide alternative routes to the pyridyl nucleus and further substitution thereof.

Scheme 3

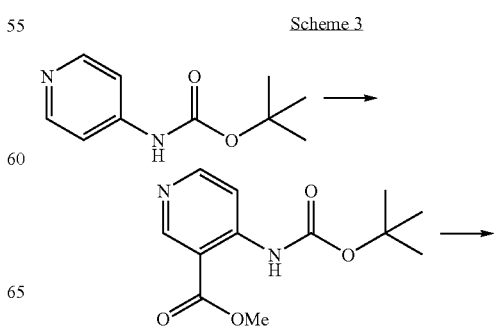

-continued

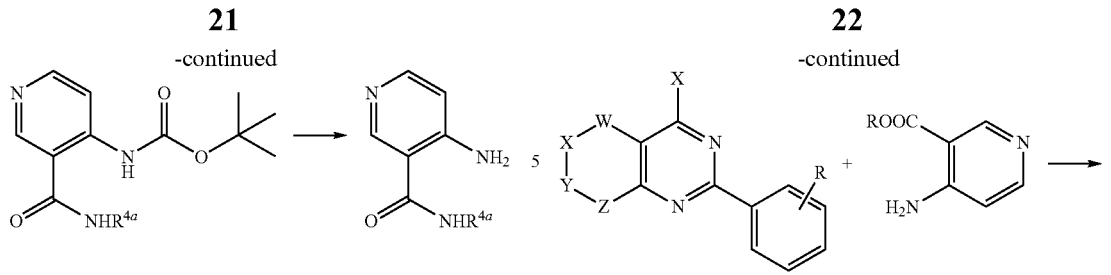

Scheme 4

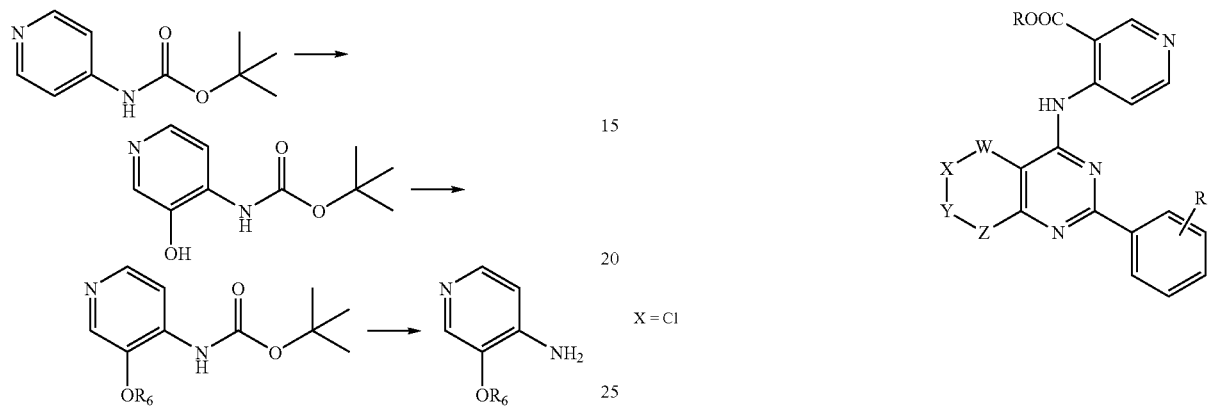

Scheme 5:
General method for attaching a 4-aminopyridine to a bicyclic pyrimidine.

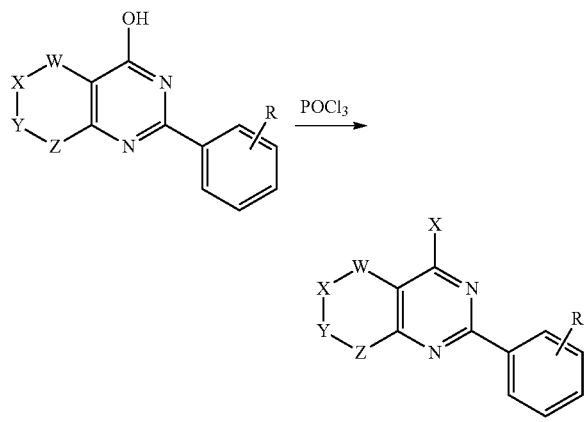

Scheme 1 shows how a 4-hydroxy pyrimidine can be converted into a 4-halo pyrimidine, which is then coupled to a 4-aminopyridine. The coupling is done using a palladium catalyst, and may be done with the 4-chloropyrimidine derivative in some cases, but was done with the 4-iodo derivative in some cases.

The requisite 3-carboxamide group may be present on the 4-aminopyridine when the pyridine is added to the pyrimidine, or the pyridyl group may contain an ester at the 3-position as illustrated in Scheme 5. In that case, the ester can be hydrolyzed with base to form a carboxylic acid after the pyridine group is installed. This carboxylic acid is readily coupled to a wide variety of amine groups by methods well known in the art for forming amide bonds as illustrated in Scheme 2. Because of the wide variety of amines that are available and the generality of this amide formation reaction, this method provides access to a tremendous variety of compounds of the present invention.

Compounds embodied in the present invention are shown below in Table 1:

TABLE 1

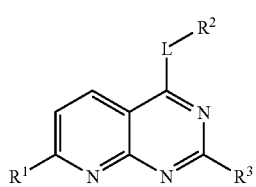

(I)

| # | $R^1$ | L | $R^2$ | $R^3$ |
|---|---|---|---|---|
| 1 | H | ![Boc-N structure] | ![pyridyl structure] | ![chlorofluorophenyl structure] |

TABLE 1-continued
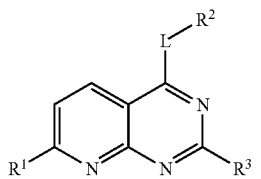
(I)
| # | R¹ | L | R² | R³ |
|---|----|---|----|----|
| 2 | H | —NH— | 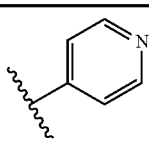 | 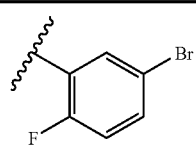 |
| 3 | H | —NH— | 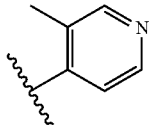 | 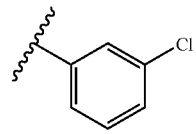 |
| 4 | 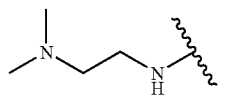 | —NH— | 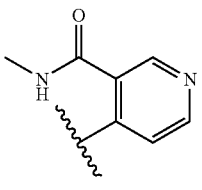 | 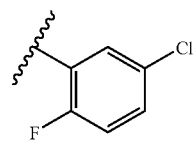 |
| 5 | H | —NH— | 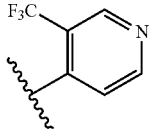 | 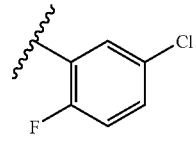 |
| 6 | H | —NH— | 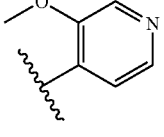 | 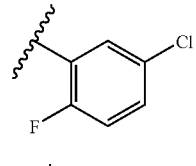 |
| 7 | H | —NH— | 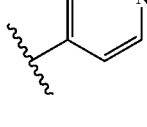 | 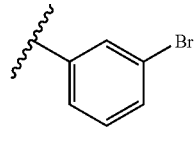 |
| 8 | H | —NH— | 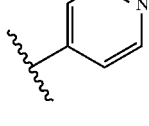 | 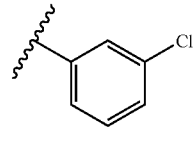 |
| 9 | —NH₂ | —NH— | 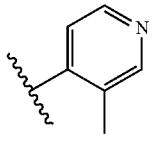 | 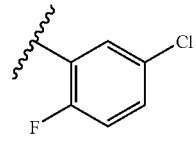 |
| 10 | H | —NH— | 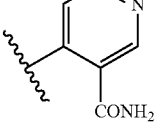 | 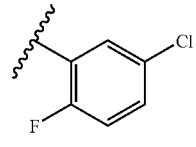 |

TABLE 1-continued (I)

| # | R¹ | L | R² | R³ |
|---|----|----|----|----|
| 11 | H | —NH— | 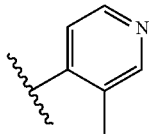 3-methylpyridin-4-yl | 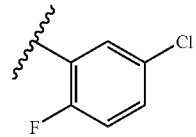 5-chloro-2-fluorophenyl |
| 12 | H | —NH— | 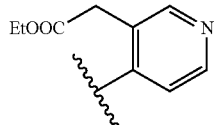 3-(ethoxycarbonylmethyl)pyridin-4-yl | 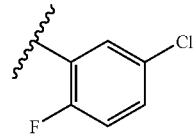 5-chloro-2-fluorophenyl |
| 13 | 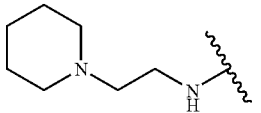 2-(piperidin-1-yl)ethylamino | —NH— | 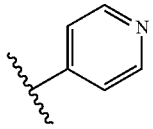 pyridin-4-yl | 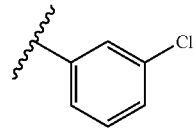 3-chlorophenyl |
| 14 | 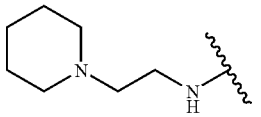 2-(piperidin-1-yl)ethylamino | —NH— | 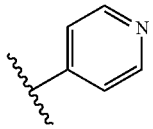 pyridin-4-yl | 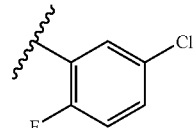 5-chloro-2-fluorophenyl |
| 15 | —NH₂ | —NH— | 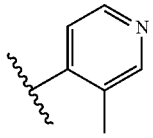 3-methylpyridin-4-yl | 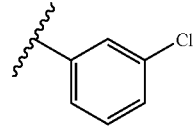 3-chlorophenyl |
| 16 | H | —NH— | 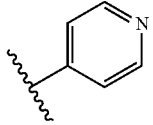 pyridin-4-yl | 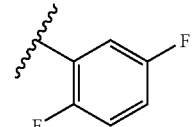 2,5-difluorophenyl |
| 17 | —NH₂ | —NH— | 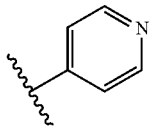 pyridin-4-yl | 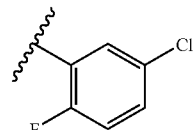 5-chloro-2-fluorophenyl |
| 18 | 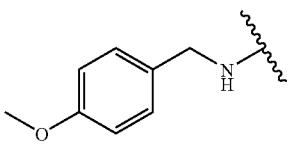 4-methoxybenzylamino | —NH— | 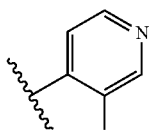 3-fluoropyridin-4-yl | 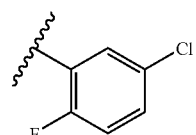 5-chloro-2-fluorophenyl |
| 19 | 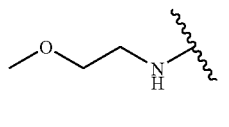 2-methoxyethylamino | —NH— | 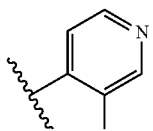 3-fluoropyridin-4-yl | 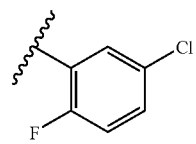 5-chloro-2-fluorophenyl |

TABLE 1-continued
| # | R¹ | L | R² | R³ |
|---|----|----|----|-----|
| 20 | 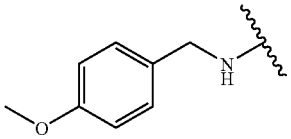 | —NH— | 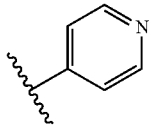 | 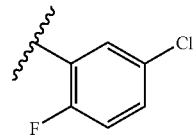 |
| 21 | H | —NH— | 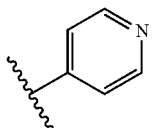 | 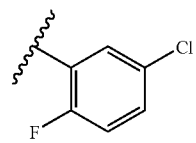 |
| 22 | H | —NH— | 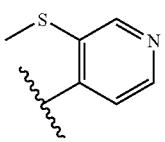 | 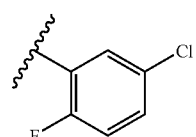 |
| 23 | 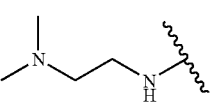 | —NH— | 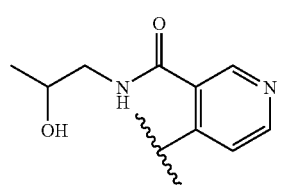 | 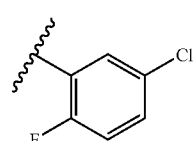 |
| 24 | 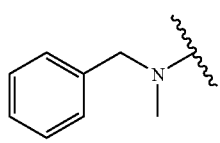 | —NH— | 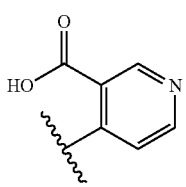 | 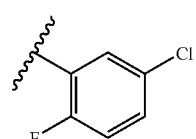 |
| 25 | 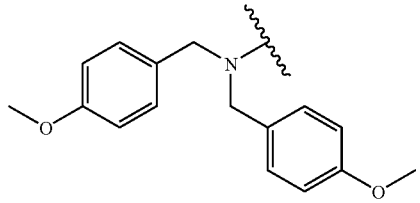 | —NH— | 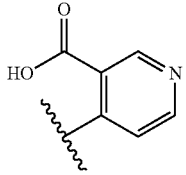 | 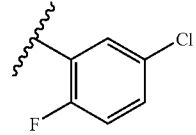 |
| 26 | H | —NH— | 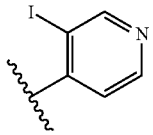 | 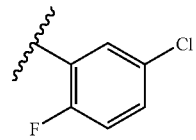 |

TABLE 1-continued (I)

| # | R¹ | L | R² | R³ |
|---|---|---|---|---|
| 27 | —NH₂ | —NH— | N-methyl pyridine-3-carboxamide (4-yl attachment) | 5-chloro-2-fluorophenyl |
| 28 | N-benzyl-N-methylamino | —NH— | methyl pyridine-3-carboxylate (4-yl attachment) | 5-chloro-2-fluorophenyl |
| 29 | —NH₂ | —NH— | 3-fluoropyridin-4-yl | 5-chloro-2-fluorophenyl |
| 30 | 2-methoxyethylamino | —NH— | N-methyl pyridine-3-carboxamide (4-yl attachment) | 5-chloro-2-fluorophenyl |
| 31 | 2-(dimethylamino)ethylamino | —NH— | 3-fluoropyridin-4-yl | 5-chloro-2-fluorophenyl |
| 32 | H | —NH— | N-methyl pyridine-3-carboxamide (4-yl attachment) | 5-chloro-2-fluorophenyl |
| 33 | H | —NH— | pyridin-4-yl | 3-chlorophenyl |
| 34 | H | —NH— | methyl pyridine-3-carboxylate (4-yl attachment) | 5-chloro-2-fluorophenyl |

TABLE 1-continued (I)

| # | R¹ | L | R² | R³ |
|---|----|---|----|----|
| 35 | —NH₂ | —NH— | 4-pyridyl | 3-chlorophenyl |
| 36 | —NH₂ | —NH— | 3-fluoro-4-pyridyl | 5-chloro-2-fluorophenyl |
| 37 | (CH₃)₂N-CH₂CH₂-NH— | —NH— | N-methyl-pyridine-3-carboxamide-4-yl | 5-chloro-2-fluorophenyl |

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

It should be noted that the compounds of the invention can be administered as individual active ingredients, or as mixtures of several embodiments of this formula. In addition, the compounds of the invention may be used as single therapeutic agents or in combination with other therapeutic agents.

Due to their favorable antiviral properties, as will be apparent from the examples, the compounds of the present invention are useful in the treatment of individuals infected by HCV and for the prophylaxis of these individuals. In general, the compounds of the present invention may be useful in the treatment of warm-blooded animals infected with flaviviruses. Conditions which may be prevented or treated with the compounds of the present invention, especially conditions associated with HCV and other pathogenic flaviviruses, such as Yellow fever, Dengue fever (types 1-4), St. Louis encephalitis, Japanese encephalitis, Murray valley encephalitis, West Nile virus and Kunjin virus. The conditions associated with HCV include progressive liver fibrosis, inflammation and necrosis leading to cirrhosis, end-stage liver disease, and HCC; and for the other pathogenic flaviruses the conditions include yellow fever, dengue fever, haemorraghic fever and encephalitis.

The compounds of the present invention or any subgroup thereof may therefore be used as medicines against the above-mentioned conditions. Said use as a medicine or method of treatment comprises the systemic administration to HCV-infected subjects of an amount effective to combat the conditions associated with HCV and other pathogenic flaviviruses. Consequently, the compounds of the present invention can be used in the manufacture of a medicament useful for treating conditions associated with HCV and other pathogenic flaviviruses.

In an embodiment, the invention relates to the use of a compound of formula (V) or any subgroup thereof as defined herein in the manufacture of a medicament for treating or combating infection or disease associated with HCV infection in a mammal. The invention also relates to a method of treating a flaviviral infection, or a disease associated with flavivirus infection comprising administering to a mammal in need thereof an effective amount of a compound of formula (V) or a subgroup thereof as defined herein.

In another embodiment, the present invention relates to the use of formula (V) or any subgroup thereof as defined herein for the manufacture of a medicament useful for inhibiting HCV activity in a mammal infected with flaviviruses, in particular HCV.

In another embodiment, the present invention relates to the use of formula (V) or any subgroup thereof as defined herein for the manufacture of a medicament useful for inhibiting HCV activity in a mammal infected with flaviviruses, wherein said HCV is inhibited in its replication.

Also, the combination of previously known anti-HCV compound, such as, for instance, interferon-α (IFN-α), pegylated interferon-α and/or ribavirin, and a compound of the present invention can be used as a medicine in a combination therapy. The term "combination therapy" relates to a product containing mandatory (a) a compound of the present invention, and (b) optionally another anti-HCV compound, as a combined preparation for simultaneous, separate or sequential use in treatment of HCV infections, in particular, in the treatment of infections with HCV type 1. Thus, to combat or treat HCV infections, the compounds of this invention may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (V) or any subgroup thereof as defined above for the manufacture of a medicament useful for inhibiting HCV activity in a mammal infected with HCV viruses, wherein said medicament is used in a combination therapy, said combination therapy preferably comprising a compound of formula (V) and (pegylated) IFN-α and/or ribavirin.

It will be appreciated by the person skilled in the art that the compounds of formula (V) may be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

All patents, patent applications and articles referred to before or below are incorporated herein by reference.

EXAMPLES

The following examples are intended to illustrate, but not to limit the invention.

Example 1

Synthesis of pyrido[2,3-d]pyrimidines

The molecules described in the present invention may be synthesized according to the procedures described in WO03/097615, in particular by the reaction scheme 4.

Example 2

Activity of Compounds of Formula (V) in HCV Replicon Assays

Stable Replicon Cell Reporter Assays:
The compounds of the present invention were examined for activity in the inhibition of HCV RNA replication in a cellular assay. The assay demonstrated that the present compounds exhibit activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbored an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct was bordered by 5' and 3' NTRs (non-translated regions) from HCV type 1b. Continued culture of the replicon cells in the presence of G418 (neo$^R$) was dependent on the replication of the HCV RNA. The stably transfected replicon cells that expressed HCV RNA, which replicated autonomously and to high levels, encoding inter alia luciferase, were used for screening the antiviral compounds.

Cellular Assay Experimental Method:
The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures had high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

The compounds tested were found to have activities as follows:

TABLE 3

| Compound Number | HCV Replicon activity (μM) |
| --- | --- |
| 1 | 0.13 |
| 2 | 0.23 |
| 3 | 0.41 |
| 4 | >10 |
| 5 | 25 |
| 6 | 0.56 |
| 7 | 0.57 |
| 8 | 0.57 |
| 9 | 0.67 |
| 10 | 0.76 |
| 11 | 0.77 |
| 12 | 1.1 |
| 13 | 1.3 |
| 14 | 1.6 |
| 15 | 1.8 |
| 16 | 2.1 |
| 17 | 2.2 |
| 18 | 5.1 |
| 19 | 3.4 |
| 20 | 3.9 |
| 21 | 3.2 |
| 22 | 0.49 |
| 23 | >10 |
| 24 | >10 |
| 25 | >10 |
| 26 | 0.48 |
| 27 | >10 |
| 28 | >10 |
| 29 | >10 |
| 30 | >10 |
| 31 | >10 |
| 32 | 12 |
| 33 | 15 |
| 34 | 19 |
| 35 | 12 |
| 36 | >10 |
| 37 | >10 |

The invention claimed is:

1. A method of inhibiting HCV replication in a mammal infected with HCV, wherein said method comprises the administration of an effective amount of a HCV inhibitory compound, said compound having the formula (I)

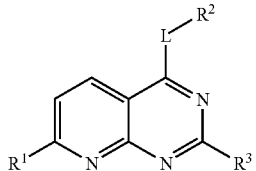

(I)

or an N-oxide, salt, stereoisomeric form, racemic mixture, prodrug, or ester thereof, wherein $R^1$ is hydrogen, amino, mono- or disubstituted amino, wherein the substituent(s) of the amino may be selected from $C_{1-6}$alkyl, $C_{2-6}$alkenyl, $C_{2-6}$alkynyl, $C_{1-4}$alkyloxy$C_{1-4}$alkyl, di$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkyl, or $C_{1-4}$alkoxy;

L is —$NR^8$—, —$NR^8$—$C_{1-6}$alkanediyl-, —$NR^8$—CO—$C_{1-6}$alkanediyl-, —$NR^8$—$SO_2$—$C_{1-6}$alkanediyl-, —O—, —O—$C_{1-6}$alkanediyl-, —O—CO—, —O—CO—$C_{1-6}$alkanediyl-, —S—, —S—$C_{1-6}$alkanediyl-, or

wherein the dotted ring together with N and Z form a $Het^1$ cycle having 5 to 8 members including ring members N and Z, and wherein said L ring is attached to the pyrido[2,3-d]pyrimidine ring by the nitrogen atom;

Z represents N or CH;

$R^2$ represents hydrogen, hydroxy$C_{1-6}$alkyl, $C_{3-7}$cycloalkyl, aryl, $Het^1$, or $Het^2$, wherein said $C_{3-7}$cycloalkyl, aryl, $Het^1$, and $Het^2$ are each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, $NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, and aminophenylcarbonyl, and wherein the $C_{1-4}$alkyl may be further substituted with —$COOR^7$;

$R^3$ represents $C_{1-6}$alkyl, $C_{3-7}$cycloalkyl, aryl, aryl$C_{1-6}$alkyl, $Het^1$, $Het^2$ or $Het^2C_{1-6}$alkyl, each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}COOR^7$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, and —$SO_2NR^{4a}R^{4b}$;

each $R^{4a}$ and $R^{4b}$ is independently hydrogen, $C_{1-4}$alkyl, hydroxy$C_{1-4}$alkyl, $Het^1C_{1-4}$alkyl, polyhalo$C_{1-4}$alkyl, cyano, or nitro;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl; and each $R^8$ is independently hydrogen, $C_{1-10}$alkyl, $C_{2-10}$alkenyl, $C_{2-10}$alkynyl, $C_{1-10}$alkylcarbonyl, amino$C_{1-10}$alkyl, aryl, arylcarbonyl, aryl$C_{1-10}$alkyl, $Het^1$, $Het^1C_{1-6}$alkyl, or a nitrogen-protecting group, wherein the aryl is optionally substituted with 1 to 3 substituents selected from $C_{1-4}$alkyl, $C_{2-4}$alkenyl, $C_{2-4}$alkynyl, $C_{1-4}$alkylcarbonyl, phenyl, $C_{1-4}$alkylphenyl, phenylcarbonyl, aminophenyl, amino$C_{1-4}$alkylphenyl, aminophenylcarbonyl, halo, —$OR^6$, —$NR^{4a}R^{4b}$, —$SR^5$, —$SOR^5$, —$NR^{4a}SOR^5$, —$NR^{4a}SO_2R^5$, —$SO_2R^5$, —$OCOR^6$, —$NR^{4a}COR^6$, —NR$^{4a}$CONR$^{4a}$R$^{4b}$, —NR$^{4a}$COOR$^6$, —OCONR$^{4a}$R$^{4b}$, —COOR$^6$, —SO$_3$R$^6$, —CONR$^{4a}$R$^{4b}$, —SO$_2$NR$^{4a}$R$^{4b}$, cyano, polyhaloC$_{1-4}$alkyl, and nitro;

Het$^1$ is defined as a saturated or partially unsaturated monocyclic, bicyclic or tricyclic heterocycle having ring member sizes selected from the group consisting of 3 to 12 ring members, 5 to 10 ring members and 5 to 8 ring members, which contains one or more heteroatom ring members selected from nitrogen, oxygen or sulfur and which is optionally substituted on one or more carbon atoms by C$_{1-6}$alkyl, C$_{1-6}$alkyloxy, halo, hydroxy, oxo, optionally mono- or disubstituted amino, nitro, cyano, polyhaloC$_{1-4}$alkyl, carboxyl, C$_{1-6}$alkoxycarbonyl, C$_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are hydrogen, or C$_{1-4}$alkyl;

Het$^2$ is defined as an aromatic monocyclic, bicyclic or tricyclic heterocycle having ring member sizes selected from the group consisting of 5 to 14 ring members, 5 to 10 ring members and 5 to 6 ring members, which contains one or more heteroatom ring members each independently selected from nitrogen, oxygen or sulfur, and which is optionally substituted on one or more carbon atoms by C$_{1-6}$alkyl, optionally mono- or disubstituted aminoC$_{1-6}$alkyl, hydroxyC$_{1-6}$alkyl, C$_{1-6}$alkyloxy, halo, hydroxy, optionally mono- or disubstituted amino, nitro, cyano, polyhaloC$_{1-4}$alkyl, carboxyl, C$_{1-6}$alkoxycarbonyl, C$_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 5 to 12 ring members; whereby the optional substituents on any amino function are hydrogen, or C$_{1-4}$alkyl;

aryl is defined as phenyl.

2. The method of inhibiting HCV replication according to claim 1, wherein the compound has the formula (II)

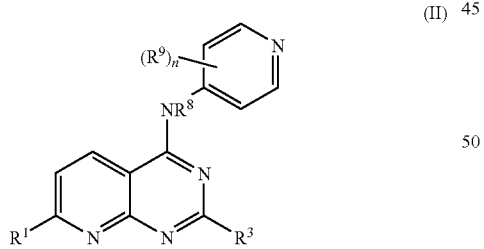

(II)

or an N-oxide, salt, stereoisomeric form, racemic mixture, prodrug, or ester thereof, and further wherein R$^9$ represents C$_{1-4}$alkyl, C$_{2-4}$alkenyl, C$_{2-4}$alkynyl, polyhaloC$_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, —SO$_2$NR$^{4a}$R$^{4b}$, morpholin-4-yl, phenyl, aminophenyl, or aminophenyl-carbonyl, and wherein the C$_{1-4}$alkyl may be further substituted with —COOR$^7$; and n is 0, 1, 2, 3, or 4.

3. The method of inhibiting HCV replication of claim 1, wherein the compound has the formula (III)

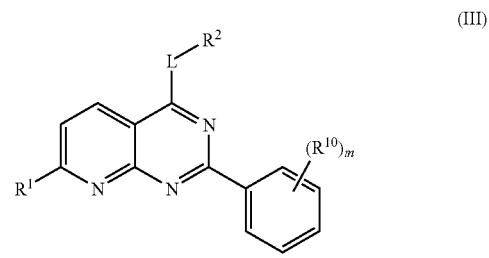

(III)

or an N-oxide, salt, stereoisomeric form, racemic mixture, prodrug, or ester thereof, and further wherein R$^{10}$ represents C$_{1-4}$alkyl, C$_{2-4}$alkenyl, C$_{2-4}$alkynyl, polyhaloC$_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$COOR$^7$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, and —SO$_2$NR$^{4a}$R$^{4b}$; and m is 0, 1, 2, 3, or 4.

4. The method of inhibiting HCV replication according to claim 3, wherein the compound has the formula (IV)

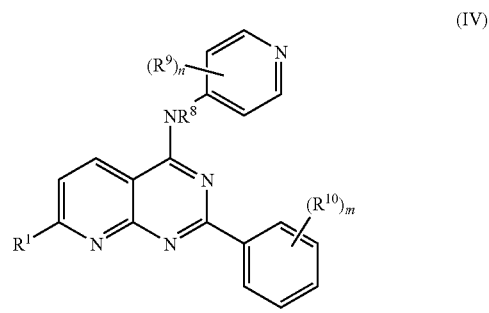

(IV)

or an N-oxide, salt, stereoisomeric form, racemic mixture, prodrug, or ester thereof, and further wherein R$^9$ represents C$_{1-4}$alkyl, C$_{2-4}$alkenyl, C$_{2-4}$alkynyl, polyhaloC$_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, —SO$_2$NR$^{4a}$R$^{4b}$, morpholin-4-yl, phenyl, aminophenyl, or aminophenyl-carbonyl, and wherein the C$_{1-4}$alkyl may be further substituted with —COOR$^7$; and n is 0, 1, 2, 3, or 4.

5. The method of inhibiting HCV replication according to claim 1, wherein the compound has the formula (V)

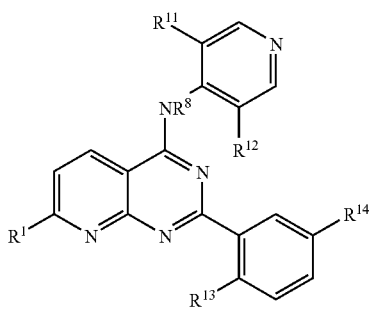

or an N-oxide, salt, stereoisomeric form, racemic mixture, prodrug, or ester thereof, and further wherein each $R^{11}$ and $R^{12}$ represent, independently, hydrogen, $C_{1-4}$alkyl, $C_{2-4}$alkenyl, $C_{2-4}$alkynyl, polyhalo$C_{1-4}$alkyl, halo, cyano, nitro, —$COR^6$, —$COOR^7$, —$CONR^{4a}R^{4b}$, —$OR^7$, —$OCOR^6$, —$OCONR^{4a}R^{4b}$, —$NR^{4a}R^{4b}$, —$NR^{4a}COR^6$, —$NR^{4a}CONR^{4a}R^{4b}$, —$NR^{4a}SOR^5$, —$NR^{4a}SO_2R^5$, —$SR^5$, —$SOR^7$, —$SO_2R^5$, —$SO_3R^7$, —$SO_2NR^{4a}R^{4b}$, morpholin-4-yl, phenyl, aminophenyl, or aminophenylcarbonyl, and wherein the $C_{1-4}$alkyl may be further substituted with —$COOR^7$;

$R^{13}$ represents hydrogen, or halo; and $R^{14}$ represents halo.

6. The method of inhibiting HCV replication according to claim 5, wherein $R^1$ is hydrogen, amino, mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$ and $R^{4b}$ is independently hydrogen, or $C_{1-4}$alkyl;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, polyhalo$C_{1-4}$alkyl, halo, —$COR^6$, —$COOR^7$, —$OR^7$, —$NR^{4a}R^{4b}$, —$NR^{4a}SO_2R^5$, —$SR^5$, —$SO_2R^5$, or —$SO_2NR^{4a}R^{4b}$;

$R^{13}$ represents hydrogen, or halo; and $R^{14}$ represents halo.

7. The method of inhibiting HCV replication according to claim 5, wherein $R^1$ is hydrogen, amino, mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, polyhalo$C_{1-4}$alkyl, halo, —$COR^6$, —$COOR^7$, —$OR^7$, —$SR^5$;

$R^{13}$ represents hydrogen, or halo; and $R^{14}$ represents halo.

8. The method of inhibiting HCV replication according to claim 5, wherein $R^1$ is hydrogen, amino, monosubstituted amino, wherein the substituents of the amino may be selected from $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkoxy;

each $R^5$ is $C_{1-4}$alkyl;

each $R^7$ is $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, polyhalo$C_{1-4}$alkyl, halo, —$COOR^7$, —$OR^7$, —$SR^5$;

$R^{13}$ represents hydrogen, or halo; and $R^{14}$ represents halo.

9. The method of inhibiting HCV replication according to claim 5, wherein $R^1$ is hydrogen, amino, monosubstituted amino, wherein the substituents of the amino may be selected from $C_{1-4}$alkyloxy$C_{1-4}$alkyl, piperidin-1-yl-$C_{1-4}$alkyl, phenyl$C_{1-6}$alkyl, wherein the phenyl group may be further substituted with $C_{1-4}$alkoxy;

each $R^5$ is $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —$COOR^7$, halo, —$OR^7$, or —$SR^5$;

$R^{13}$ represents hydrogen, or halo; and $R^{14}$ represents halo.

10. The method of inhibiting HCV replication according to claim 1, wherein $R^1$ is hydrogen, or amino;

each $R^5$ is $C_{1-4}$alkyl;

$R^8$ is hydrogen, or a nitrogen-protecting group;

each $R^{11}$ and $R^{12}$ represent, independently, hydrogen, $C_{1-4}$alkyl, —$OR^7$, or —$SR^5$;

$R^{13}$ represents hydrogen, or halo; and $R^{14}$ represents halo.

11. The method of inhibiting HCV replication according to claim 1, wherein the nitrogen-protecting group is $C_{1-6}$alkyloxycarbonyl, arylmethoxycarbonyl, trifluoroacetyl, or arylmethyl.

12. The method of inhibiting HCV replication according to claim 1, wherein the nitrogen-protecting group is t-butoxycarbonyl, benzyloxycarbonyl, benzyl, or trifluoromethyl.

13. A compound of the formula (V)

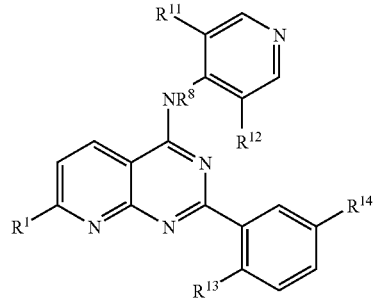

or an N-oxide, salt, stereoisomeric form, racemic mixture, prodrug, or ester thereof, wherein R¹ is amino, or mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$ and $R^{4b}$ is independently hydrogen, or $C_{1-4}$alkyl;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —COOR⁷, polyhalo$C_{1-4}$alkyl, halo, —COR⁶, —OR⁷, —NR$^{4a}$R$^{4b}$, —NR$^{4a}$SO₂R⁵, —SR⁵, —SO₂R⁵, or —SO₂NR$^{4a}$R$^{4b}$;

$R^{13}$ represents hydrogen, or halo; and $R^{14}$ represents halo.

14. A compound according to claim 13, wherein

R¹ is amino, or mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$, $R^{4b}$, $R^5$, $R^7$, independently, is hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl, halo, —OR⁷, or —SR⁵;

$R^{13}$ represents hydrogen, or halo; and $R^{14}$ represents halo.

15. A compound according to claim 13, wherein

R¹ is amino;

each $R^{4a}$, $R^{4b}$, $R^5$, $R^7$, independently, is hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl, halo, —OR⁷, or —SR⁵;

$R^{13}$ represents hydrogen, or halo; and $R^{14}$ represents halo.

16. A compound according to claim 13, wherein $R^{11}$ is hydrogen; and $R^{12}$ is $C_{1-4}$alkyl, halo, $C_{1-4}$alkoxy, $C_{1-4}$alkylthio, or trifluoromethyl.

17. A compound according to claim 13, wherein $R^{13}$ and $R^{14}$ represent halo.

18. A compound according to claim 13, wherein the nitrogen-protecting group is $C_{1-6}$alkyloxycarbonyl, arylmethoxycarbonyl, trifluoroacetyl, or arylmethyl.

19. A compound according to claim 13, wherein the nitrogen-protecting group is t-butoxycarbonyl, benzyloxycarbonyl, benzyl, or trifluoromethyl.

20. A pharmaceutical composition comprising a compound of formula (V)

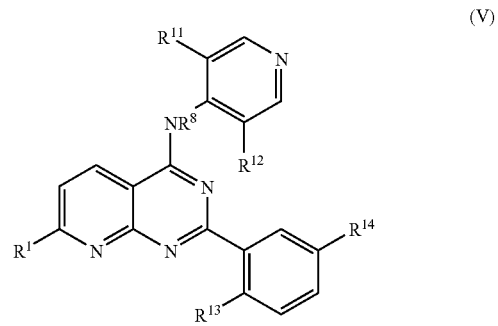

(V)

or an N-oxide, salt, stereoisomeric form, racemic mixture, prodrug, or ester thereof, wherein R¹ is amino, or mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$ and $R^{4b}$ is independently hydrogen, or $C_{1-4}$alkyl;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —COOR⁷, polyhalo$C_{1-4}$alkyl, halo, —COR⁶, —OR⁷, —NR$^{4a}$R$^{4b}$, —NR$^{4a}$SO₂R⁵, —SR⁵, —SO₂R⁵, or —SO₂NR$^{4a}$R$^{4b}$;

$R^{13}$ represents hydrogen, or halo;

$R^{14}$ represents halo; and at least one pharmaceutically acceptable excipient.

21. A pharmaceutical composition comprising a compound of formula (V)

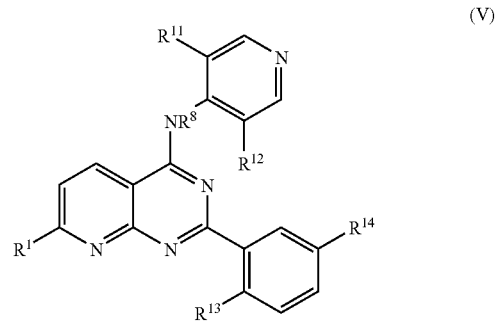

(V)

or an N-oxide, salt, stereoisomeric form, racemic mixture, prodrug, or ester thereof, wherein R¹ is amino, or mono- or disubstituted amino, wherein the substituents of the amino may be selected from $C_{1-6}$alkyl, $C_{1-4}$alkyloxy$C_{1-4}$alkyl, di$C_{1-4}$alkylamino$C_{1-4}$alkyl, piperidin-1-yl-$C_{1-4}$alkyl, phenyl$C_{1-6}$alkyl, wherein the phenyl group may be further substituted with $C_{1-4}$alkyl, or $C_{1-4}$alkoxy;

each $R^{4a}$ and $R^{4b}$ is independently hydrogen, or $C_{1-4}$alkyl;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl;

$R^8$ is hydrogen, or a nitrogen-protecting group;

each $R^{11}$ and $R^{12}$ represent, independently, hydrogen, $C_{1-4}$alkyl which may be further substituted with —COOR$^7$, polyhalo$C_{1-4}$alkyl, halo, —COR$^6$, —OR$^7$, —NR$^{4a}$R$^{4b}$, —NR$^{4a}$SO$_2$R$^5$, SR$^5$, —SO$_2$R$^5$, or —SO$_2$NR$^{4a}$R$^{4b}$;

$R^{13}$ represents hydrogen, or halo;

$R^{14}$ represents halo, and further comprising one or more other anti-HCV agents.

22. A method of treating a mammal infected with HCV, wherein said method comprises the administration of an effective amount of a HCV inhibitory compound, said compound having the formula (I)

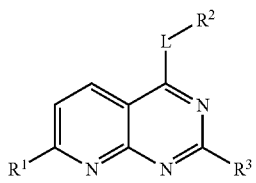

(I)

or an N-oxide, salt, stereoisomeric form, racemic mixture, prodrug, or ester thereof, wherein $R^1$ is hydrogen, amino, mono- or disubstituted amino, wherein the substituent(s) of the amino may be selected from $C_{1-6}$alkyl, $C_{2-6}$alkenyl,
  $C_{2-6}$alkynyl, $C_{1-4}$alkyloxy$C_{1-4}$alkyl, di$C_{1-4}$alkylamino$C_{1-4}$alkyl, piperidin-1-yl-$C_{1-4}$alkyl, aryl$C_{1-6}$alkyl, wherein the aryl group may be further substituted with $C_{1-4}$alkyl, or $C_{1-4}$alkoxy;

L is —NR$^8$—, —NR$^8$—$C_{1-6}$alkanediyl-, —NR$^8$—CO—$C_{1-6}$alkanediyl-, —NR$^8$—SO$_2$—$C_{1-6}$alkanediyl-, —O—, —O—$C_{1-6}$alkanediyl-, —O—CO—, —O—CO—$C_{1-6}$alkanediyl-, —S—, —S—$C_{1-6}$alkanediyl-, or

wherein the dotted ring together with N and Z form a Het$^1$ cycle having 5 to 8 members including ring members N and Z, and wherein said L ring is attached to the pyrido[2,3-d]pyrimidine ring by the nitrogen atom;

Z represents N or CH;

$R^2$ represents hydrogen, hydroxy$C_{1-6}$alkyl, $C_{3-7}$cycloalkyl, aryl, Het$^1$, or Het$^2$, wherein said $C_{3-7}$cycloalkyl, aryl, Het$^1$, and Het$^2$ are each independently optionally substituted with one or more substituents selected from $C_{1-4}$alkyl, $C_{2-4}$alkenyl,
  $C_{2-4}$alkynyl, polyhalo$C_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, —SO$_2$NR$^{4a}$R$^{4b}$, morpholin-4-yl, phenyl, aminophenyl, and aminophenylcarbonyl, and wherein the $C_{1-4}$alkyl may be further substituted with —COOR$^7$;

$R^3$ represents $C_{1-6}$alkyl, $C_{3-7}$cycloalkyl, aryl, aryl$C_{1-6}$alkyl, Het$^1$, Het$^2$ or Het$^2$$C_{1-6}$alkyl, each independently optionally substituted with one or more substituents selected from $C_{1-4}$alkyl, $C_{2-4}$alkenyl, $C_{2-4}$alkynyl, polyhalo$C_{1-4}$alkyl, halo, cyano, nitro, —COR$^6$, —COOR$^7$, —CONR$^{4a}$R$^{4b}$, —OR$^7$, —OCOR$^6$, —OCONR$^{4a}$R$^{4b}$, —NR$^{4a}$R$^{4b}$, —NR$^{4a}$COR$^6$, —NR$^{4a}$COOR$^7$, —NR$^{4a}$CONR$^{4a}$R$^{4b}$, —NR$^{4a}$SOR$^5$, —NR$^{4a}$SO$_2$R$^5$, —SR$^5$, —SOR$^7$, —SO$_2$R$^5$, —SO$_3$R$^7$, and —SO$_2$NR$^{4a}$R$^{4b}$;

each $R^{4a}$ and $R^{4b}$ is independently hydrogen, $C_{1-4}$alkyl, hydroxy$C_{1-4}$alkyl, Het$^1$$C_{1-4}$alkyl, polyhalo$C_{1-4}$alkyl, cyano, or nitro;

each $R^5$ is independently hydrogen, or $C_{1-4}$alkyl;

each $R^6$ is independently hydrogen, or $C_{1-4}$alkyl;

each $R^7$ is independently hydrogen, or $C_{1-4}$alkyl; and each $R^8$ is independently hydrogen, $C_{1-10}$alkyl, $C_{2-10}$alkenyl, $C_{2-10}$alkynyl,
  $C_{1-10}$alkylcarbonyl, amino$C_{1-10}$alkyl, aryl, arylcarbonyl, aryl$C_{1-10}$alkyl, Het$^1$, Het$^1$$C_{1-6}$alkyl, or a nitrogen-protecting group, wherein the aryl is optionally substituted with 1 to 3 substituents selected from $C_{1-4}$alkyl, $C_{2-4}$alkenyl,
  $C_{2-4}$alkynyl, $C_{1-4}$alkylcarbonyl, phenyl, $C_{1-4}$alkylphenyl, phenylcarbonyl, aminophenyl, amino$C_{1-4}$alkylphenyl, aminophenylcarbonyl, halo, —OR$^6$, —NR$^{4a}$R$^{4b}$, —SR$^5$, —SOR$^5$, —NR$^{4a}$SOR$^5$, —NR$^{4a}$SO$_2$R$^5$, —SO$_2$R$^5$, —OCOR$^6$, —NR$^{4a}$COR$^6$, —NR$^{4a}$CONR$^{4a}$R$^{4b}$, —NR$^{4a}$COOR$^6$, —OCONR$^{4a}$R$^{4b}$, COOR$^6$, —SO$_3$R$^6$, —CONR$^{4a}$R$^{4b}$, —SO$_2$NR$^{4a}$R$^{4b}$, cyano, polyhalo$C_{1-4}$ alkyl, and nitro;

Het$^1$ is defined as a saturated or partially unsaturated monocyclic, bicyclic or tricyclic heterocycle having ring member sizes selected from the group consisting of 3 to 12 ring members, 5 to 10 ring members and 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halo, hydroxy, oxo, optionally mono- or disubstituted amino, nitro, cyano, polyhalo$C_{1-4}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are hydrogen, or $C_{1-4}$alkyl;

Het$^2$ is defined as an aromatic monocyclic, bicyclic or tricyclic heterocycle having ring member sizes selected from the group consisting of 5 to 14 ring members, 5 to 10 ring members and 5 to 6 ring members, which contains one or more heteroatom ring members each independently selected from nitrogen, oxygen or sulfur, and which is optionally substituted on one or more carbon atoms by $C_{1-6}$alkyl, optionally mono- or disubstituted amino$C_{1-6}$alkyl, hydroxy$C_{1-6}$alkyl, $C_{1-6}$alkyloxy, halo, hydroxy, optionally mono- or disubstituted amino, nitro, cyano, polyhalo-$C_{1-4}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 5 to 12 ring members; whereby the optional substituents on any amino function are hydrogen, or $C_{1-4}$alkyl;

aryl is defined as phenyl.

* * * * *